United States Patent
Beilinson et al.

(10) Patent No.: US 12,173,293 B2
(45) Date of Patent: *Dec. 24, 2024

(54) COMPOSITIONS AND METHODS FOR INCORPORATION OF DNA INTO THE GENOME OF AN ORGANISM

(71) Applicant: AgBiome, Inc., Durham, NC (US)

(72) Inventors: Vadim Beilinson, Cary, NC (US); Rebekah Deter Kelly, Durham, NC (US); Lawrence J. Nea, Raleigh, NC (US); Rodrigo Sarria, Chapel Hill, NC (US)

(73) Assignee: AGBIOME, INC., Durham, NC (US)

( * ) Notice: Subject to any disclaimer, the term of this patent is extended or adjusted under 35 U.S.C. 154(b) by 207 days.

This patent is subject to a terminal disclaimer.

(21) Appl. No.: 17/531,325

(22) Filed: Nov. 19, 2021

(65) Prior Publication Data

US 2022/0162623 A1    May 26, 2022

Related U.S. Application Data

(60) Provisional application No. 63/116,416, filed on Nov. 20, 2020.

(51) Int. Cl.
C12N 15/82 (2006.01)

(52) U.S. Cl.
CPC ..... C12N 15/8205 (2013.01); C12N 15/8241 (2013.01)

(58) Field of Classification Search
CPC ................ C12N 15/8205; C12N 15/8241
See application file for complete search history.

(56) References Cited

U.S. PATENT DOCUMENTS

| | | | |
|---|---|---|---|
| 7,598,430 B2 | 10/2009 | Weeks et al. | |
| 8,344,208 B2 | 1/2013 | Kearney et al. | |
| 10,066,235 B2 | 9/2018 | Gilbertson et al. | |
| 10,947,556 B2 * | 3/2021 | Beilinson | C12N 15/8209 |
| 2005/0034188 A1 | 2/2005 | Weeks et al. | |
| 2007/0271627 A1 | 11/2007 | Ye et al. | |
| 2013/0078706 A1 | 3/2013 | Mullins et al. | |
| 2018/0216123 A1 * | 8/2018 | Anand | C12N 15/8202 |

FOREIGN PATENT DOCUMENTS

| | | |
|---|---|---|
| ES | 2 398 792 A1 | 10/2012 |
| WO | WO 2003/003816 | 1/2003 |
| WO | WO 2005/004585 | 1/2005 |
| WO | WO 2007/137075 A2 | 11/2007 |
| WO | WO 2016/100832 A1 | 6/2016 |
| WO | WO 2017/040343 A1 | 3/2017 |

OTHER PUBLICATIONS

LPSN-list of prokaryotic names with standing in Nomenclature database for genus of Ochrobactrum (https://lpsn.dsmz.de/genus/ochrobactrum), Accessed Feb. 6, 2024. (Year: 2024).*
Conner et al., "Intragenic vectors for gene transfer without foreign DNA," Euphytica, 2007, 154:341-353.
EBI Accession No. ADX69901, T-DNA border SEQ ID No. 42, Apr. 21, 2005 (1 p).
Haaren et al., "Mutational analysis of the conserved domains of a T-region border repeat of *Agrobacterium tumefaciens*," Plant Molecular Biology, 1989, 13:523-531.
Komori et al., "Current Status of Binary Vectors and Superbinary Vectors," Plant Physiology, Dec. 2007, 145:1155-1160.
Rudder et al., "Genome sequence of *Ensifer adhaerens* OV14 provides insights into its ability as a novel vector for the genetic transformation of plant genomes," BMC Genomics, 2014, 15:268 (17 pp).

* cited by examiner

*Primary Examiner* — David H Kruse
*Assistant Examiner* — Santosh Sharma
(74) *Attorney, Agent, or Firm* — Womble Bond Dickinson (US) LLP (57) ABSTRACT

Methods and compositions are provided which allow for genetic modification of host cells, including plants and plant cells. The various methods and composition employ a recombinant DNA construct comprising SEQ ID NO: 1 and/or 2 or active variants and fragments thereof. Such polynucleotides find use in facilitating integration of polynucleotides of interest into the DNA of a host cell, including a plant or plant cell. Vectors, host cells, bacteria and plants comprising the recombinant DNA construct or fragments thereof are provided. Further provided are methods of introducing into a host cell or a plant cell a polynucleotide of interest. The method comprises contacting the host cell with a bacterium competent for the transformation of the host cell and comprises a transformation vector comprising a recombinant DNA construct.

25 Claims, 1 Drawing Sheet
Specification includes a Sequence Listing.

COMPOSITIONS AND METHODS FOR INCORPORATION OF DNA INTO THE GENOME OF AN ORGANISM

CROSS-REFERENCE TO RELATED APPLICATIONS

This application claims priority to U.S. Provisional Application No. 63/116,416, filed Nov. 20, 2020.

STATEMENT REGARDING THE SEQUENCE LISTING

The Sequence Listing associated with this application is provided in ASCII format in lieu of a paper copy, and is hereby incorporated by reference into the specification. The ASCII copy named A101100_551_5_WO_SL.txt is 7,161 bytes in size, was created on Nov. 17, 2021, and is being submitted electronically.

FIELD OF THE INVENTION

Methods and compositions are provided for the genetic modification of host cell, including plant cells.

BACKGROUND OF THE INVENTION

*Agrobacterium tumefaciens* is a widespread naturally occurring soil bacterium that causes crown gall, and has the ability to introduce new genetic material into the plant cell (Gelvin, 2003). The genetic material that is introduced is called T-DNA (transferred DNA) which is located on a Ti plasmid. A Ti plasmid is one type of conjugative mobile plasmid. Conjugative mobile plasmids are class of circular pieces of DNA that can facilitate their transfer between organisms and can be found in many different bacteria. This natural ability of the Ti plasmid to alter the plant's genetic makeup was the foundation of plant transformation using *Agrobacterium*.

Methods are needed in the art to provide other systems that allow for bacterial mediated transformation of plants or other host cells of interest.

BRIEF SUMMARY OF THE INVENTION

Methods and compositions are provided which allow for genetic modification of host cells, including plants and plant cells. The various methods and composition employ a recombinant DNA construct comprising SEQ ID NO: 1 and/or 2 or active variants and fragments thereof. Such polynucleotides find use in facilitating integration of polynucleotides of interest into the genomic DNA of a host cell, including a plant or plant cell. Vectors, host cells, bacteria and plants and plant cells comprising the recombinant DNA construct or variants and fragments thereof are provided. Further provided are methods of introducing a polynucleotide of interest into a host cell, including a plant cell. The method comprises contacting the host cell with a bacterium competent for the transformation of the host cell, wherein the bacterium comprises a transformation vector comprising a recombinant DNA construct. Other methods comprise contacting the plant cell with a bacterium competent for the transformation of the plant cell, where the bacterium comprises a plant transformation vector comprising a recombinant DNA construct provided herein.

The present inventions now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

I. Compositions

A. DNA Integration Facilitating Sequences

Various polynucleotides that facilitate integration of a polynucleotide of interest in the DNA (i.e., genomic DNA) of a host cell, including a plant or a plant cell are provided. Such sequences are set forth in SEQ ID NO: 1 and 2 and are referred to herein as "bookend 1" and "bookend 2", respectively. These sequences are described in WO 2016/100832, which is herein incorporated by reference in its entirety. As used herein, "DNA integration facilitation" refers to the ability of a sequence to promote the integration of an operably linked sequence into genomic DNA. Various methods to assay for this activity are discussed in further detail elsewhere herein.

Fragments and variants of a DNA integration facilitating sequence can be employed in the methods and compositions disclosed herein. By "fragment" is intended a portion of the polynucleotide. Fragments of SEQ ID NO: 1 or 2 may range from 24, 23, 22, 21, 20, 19, 18, 17, 16, 15, 14, 13, 12, 11, 10, 9, 8, 7, 6, or 5 nucleotides or less. In specific embodiments, active fragments of SEQ ID NO:1 or 2 are provided and thereby continue to facilitate DNA integration. In other instances, the fragments need not retain biologically activity. Such fragments may arise after DNA integration, and thereby leaving a "footprint" of SEQ ID NO:1 or 2 within the plant genomic DNA or within the genome of the host organism. Thus, such fragments can be detected in a plant genome or the other organism's genome following the use of the integration facilitation sequences.

"Variants" is intended to mean substantially similar sequences. For polynucleotides, a variant comprises a polynucleotide having a deletion (i.e., truncations) at the 5' and/or 3' end and/or a deletion and/or addition of one or more nucleotides at one or more internal sites within SEQ ID NO: 1 or 2 and/or a substitution of one or more nucleotides at one or more sites in SEQ ID NO: 1 or 2. Naturally occurring variants or synthetically derived polynucleotides, such as those generated, for example, by using site-directed mutagenesis or gene synthesis but which still retain the ability to facilitate DNA integration. In other instances, the variants need not retain biologically activity. Such variants may arise after DNA integration, and thereby leaving a footprint of the SEQ ID NO:1 or 2 within the plant genomic DNA or the host cell's DNA. Thus, such variants can be detected in a plant genome or in the host cell genome following the use of the integration facilitation sequences.

In other embodiments, biologically active variants will have a percent identity across their full length of at least 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to the polynucleotide of any one of SEQ ID NO: 1 or 2 as determined by sequence alignment programs and parameters described elsewhere herein.

Methods for generating variants and fragments are generally known in the art. For example, methods for mutagenesis and polynucleotide alterations are well known in the art. See, for example, Kunkel (1985) *Proc. Natl. Acad. Sci. USA* 82:488-492; Kunkel et al. (1987) *Methods in Enzymol.* 154:367-382; U.S. Pat. No. 4,873,192; Walker and Gaastra, eds. (1983) *Techniques in Molecular Biology* (MacMillan Publishing Company, New York) and the references cited therein.

As used herein, an "isolated" or "purified" polynucleotide or biologically active portion thereof, is substantially or essentially free from components that normally accompany or interact with the polynucleotide as found in its naturally occurring environment. Thus, an isolated or purified polynucleotide is substantially free of other cellular material or culture medium when produced by recombinant techniques, or substantially free of chemical precursors or other chemicals when chemically synthesized. Optimally, an "isolated" polynucleotide is free of sequences (optimally protein encoding sequences) that naturally flank the polynucleotide (i.e., sequences located at the 5' and 3' ends of the polynucleotide) in the genomic DNA of the organism from which the polynucleotide is derived. For example, in various embodiments, the isolated polynucleotide can contain less than about 5 kb, 4 kb, 3 kb, 2 kb, 1 kb, 0.5 kb, or 0.1 kb of nucleotide sequence that naturally flank the polynucleotide in genomic DNA of the cell from which the polynucleotide is derived.

As used herein, a polynucleotide or polypeptide is "recombinant" when it is artificial, engineered, or derived from an artificial or engineered protein or nucleic acid. For example, a polynucleotide that is inserted into a vector or any other heterologous location, e.g., in a genome of a recombinant organism, such that it is not associated with nucleotide sequences that normally flank the polynucleotide as it is found in nature is a recombinant polynucleotide. A polypeptide expressed in vitro or in vivo from a recombinant polynucleotide is an example of a recombinant polypeptide. Likewise, a polynucleotide sequence that does not appear in nature, for example, a variant of a naturally occurring gene is recombinant.

B. Recombinant Polynucleotide Constructs

The use of the term "polynucleotide" is not intended to limit the methods and compositions to polynucleotides comprising DNA. Those of ordinary skill in the art will recognize that polynucleotides can comprise ribonucleotides and combinations of ribonucleotides and deoxyribonucleotides. Such deoxyribonucleotides and ribonucleotides include both naturally occurring molecules and synthetic analogues. The polynucleotides employed herein also encompass all forms of sequences including, but not limited to, single-stranded forms, double-stranded forms, hairpins, stem-and-loop structures, and the like.

The various polynucleotides that facilitate integration of a polynucleotide of interest into the DNA (i.e., genomic DNA) or active variants or fragments thereof can be provided in recombinant DNA constructs. Such constructs comprise SEQ ID NO: 1 and/or 2 or an active variant or fragment thereof operably linked to a polynucleotide of interest. "Operably linked" is intended to mean a functional linkage between two or more elements. Operably linked elements may be contiguous or non-contiguous. For example, in the context of a polynucleotide that facilitates DNA integration "operably linked" to the polynucleotide of interest refers to a linkage between the elements that is such as to allow for SEQ ID NO: 1, 2 or an active fragment or variant thereof to promote the integration of the polynucleotide sequence of interest into the DNA.

When the sequences that facilitate DNA integration flank the polynucleotide of interest, the bookends can be any distance from one another that allow for the integration of the polynucleotide of interest. In non-limiting embodiments, the flanking bookends are separated by at least about 25, 50, 75, 100, 200, 300, 400, 500, 600, 700, 900 nucleotide or at least 1 Kb, 2 kb, 3 kb, 4 kb, 5 kb, 6 kb, 7 kb, 10 kb, 15 kb, 20 kb, 40 kb, 60 kb or more.

Various recombinant DNA constructs can be generated employing the polynucleotide that facilitates integration of a polynucleotide of interest into the genome of a host cell. Such construct can comprise a recombinant DNA construct comprising a polynucleotide of interest operably linked to one of SEQ ID NO: 1 or SEQ ID NO:2, or an active variant or fragment thereof. In such instances, the DNA sequence that facilitates integration into the genomic DNA can be operably linked to the 5' end or to the 3' end of the polynucleotide of interest. In specific embodiments, the DNA construct comprises a polynucleotide of interest operably linked at its 3' end to SEQ ID NO: 2 or SEQ ID NO: 1 or an active variant or fragment thereof. Alternatively, the DNA construct comprises a polynucleotide of interest operably linked at its 5' end to SEQ ID NO: 2 or SEQ ID NO: 1 or an active variant or fragment thereof.

In other instances, the recombinant DNA constructs comprises a polynucleotide operably linked to the DNA integration sequences wherein the sequences that facilitate integration into the DNA flank the polynucleotide of interest. In such instances, SEQ ID NO: 1, 2, or an active variant or fragment thereof can be operably linked at the 5' end of the polynucleotide of interest and SEQ ID NO: 1, 2, or an active variant thereof can be operably linked to the 3' end of the polynucleotide of interest. In one specific embodiment, SEQ ID NO: 1 or an active variant or fragment thereof is operably linked to the 5' end of the polynucleotide of interest and SEQ ID NO: 2 or an active variant or fragment thereof is operably linked to the 3' end of the polynucleotide of interest.

In one embodiment, the DNA construct comprising the sequences that facilitate integration of the polynucleotide of interest does not contain a T-DNA border sequence.

As used herein, a T-DNA "Border sequence," e.g. right border (RB) or left border (LB), refers to a directly repeated nucleic acid sequence defining an end of the transferred DNA (T-DNA) region, typically about 24 bp in length. Border sequences are from a Ti plasmid of *Agrobacterium* spp., typically *Agrobacterium tumefaciens*.

In other embodiments, the DNA construct comprises a combination of at least one T-DNA border sequence and one or more of the sequences that facilitate integration of the polypeptide of interest (i.e., SEQ ID NO: 1 or 2 or an active variant thereof). For example, the DNA construct can comprise in a 5' to 3' orientation at least one of SEQ ID NO: 1 or 2 or an active variant thereof, a polynucleotide of interest, and a right T-DNA border. In other embodiments, the DNA construct can comprise in a 5' to 3' orientation a left T-DNA border, a polynucleotide of interest, and at least one of SEQ ID NO: 1 or 2 or an active variant thereof.

As used herein, "heterologous" in reference to a sequence is a sequence that originates from a foreign species, or, if from the same species, is modified from its native form in composition and/or genomic locus by deliberate human intervention. For example, the polynucleotide(s) that facilitates introduction of the polynucleotide sequence of interest into the genome is heterologous to the polynucleotide of interest.

i. Polynucleotides of Interest

The polynucleotide of interest (which can comprise one or more expression cassettes) can be of any length that allows for integration into the genomic DNA. In specific, non-limiting embodiments, the polynucleotide of interest can be at least about 25, 50, 100, 200, 300, 400, 500, 700, 900 nucleotide or at least 1 Kb, 2 kb, 3 kb, 4 kb, 5 kb, 6 kb, 7 kb, 8 kb, 9 kb, 10 kb, 11 kb, 12 kb, 13 kb, 14 kb, 15 kb, 20 kb, 40 kb, 60 kb or more. In other embodiments, the polynucleotide of interest is at least about 6 kb to about 15 kb, or about 6 kb to about 12 kb, or about 1 kb to about 12 kb.

Various changes in phenotype of the plant or plant cells are of interest upon introduction of the polynucleotide of interest. Such alterations include, but are not limited to, modifying the fatty acid composition in a plant, altering the amino acid content of a plant, altering a plant's pathogen defense mechanism, altering the plant's herbicide tolerance and the like. These results can be achieved by providing expression of heterologous products or increased expression of endogenous products in plants. Alternatively, the results can be achieved by providing for a reduction of expression of one or more endogenous products in the plant. These changes result in a change in phenotype of the transformed plant. To this end, the polynucleotide of interest can encode a protein or it can express a polynucleotide that acts to increase or decreases expression of a sequence of interest in the plant, and can include for example, miRNA or siRNA.

Genes of interest are reflective of the commercial markets and interests of those involved in the development of the crop. Crops and markets of interest change, and as developing nations open up world markets, new crops and technologies will emerge also.

More specific categories of transgenes, for example, include genes encoding important traits for agronomics, insect resistance, disease resistance, herbicide resistance, sterility, grain characteristics, and commercial products. Genes of interest include, generally, those involved in oil, starch, carbohydrate, or nutrient metabolism as well as those affecting kernel size, sucrose loading, and the like. See, for example, U.S. Pat. Nos. 5,703,049, 5,885,801, 5,885,802, and 5,990,389, herein incorporated by reference. Other agronomically important genes encode latex, Floury 2, growth factors, seed storage factors, and transcription factors. Insect resistance genes may encode resistance to pests such as European Corn Borer, western corn root worm, fall army worm, corn ear worm, black cut worm, cotton ball worms, stink bugs, soybean aphids, and/or nematodes, such as soybean cyst nematodes or root not nematodes, and the like. Such genes include, for example, *Bacillus thuringiensis* toxic protein genes (U.S. Pat. Nos. 5,366,892; 5,747,450; 5,736,514; 5,723,756; 5,593,881; and Geiser et al. (1986) *Gene* 48:109); and the like. Genes encoding disease resistance traits include detoxification genes, such as fumonosin (U.S. Pat. No. 5,792,931); avirulence (avr) and disease resistance (R) genes (Jones et al. (1994) *Science* 266:789; Martin et al. (1993) *Science* 262:1432; and Mindrinos et al. (1994) *Cell* 78:1089); and the like. Herbicide resistance traits may include genes coding for resistance to herbicides. Sterility genes can also be encoded in an expression cassette and provide an alternative to physical detasseling. U.S. Pat. No. 5,583,210. Other genes include kinases and those encoding compounds toxic to either male or female gametophytic development.

In other embodiments, the polynucleotide of interest may facilitate the transfer of on-agronomic traits. For example, the polynucleotide of interest can encode non-agronomic proteins including antibodies for vaccines, micronutrients folic acid, vitamin A), and bio-pharmaceutical or veterinarian drugs.

It is recognized that the methods and compositions can be employed to integrate polynucleotides of interest into organism other than plants. Thus, any sequence can be employed as a polynucleotide of interest.

ii. Expression Cassettes

One or more polynucleotides can be contained in an expression cassette for expression in the plant of interest. The cassette can include 5' and 3' regulatory sequences operably linked to a polynucleotide of interest. "Operably linked" is intended to mean a functional linkage between two or more elements. For example, an operable linkage between a polynucleotide of interest and a regulatory sequence (i.e., a promoter) is a functional link that allows for expression of the polynucleotide of interest. Operably linked elements may be contiguous or non-contiguous. When used to refer to the joining of two protein coding regions, by operably linked is intended that the coding regions are in the same reading frame. Additional gene(s) can be provided on multiple expression cassettes. Such an expression cassette is provided with a plurality of restriction sites and/or recombination sites for insertion of the polynucleotide of interest.

The expression cassette can include in the 5'-3' direction of transcription, a transcriptional initiation region (i.e., a promoter) and a polynucleotide of interest. The expression cassettes may additionally contain 5' leader sequences. Such leader sequences can act to enhance translation. The regulatory regions (i.e., promoters, transcriptional regulatory regions, and translational termination regions) and/or the polynucleotide of interest with the various expression cassettes may be native/analogous to the host cell or to each other. Alternatively, the regulatory regions and/or the polynucleotide of interest may be heterologous to the host cell or to each other.

As used herein, "heterologous" in reference to a sequence is a sequence that originates from a foreign species, or, if from the same species, is modified from its native form in composition and/or genomic locus by deliberate human intervention. For example, a promoter operably linked to a heterologous polynucleotide is from a species different from the species from which the polynucleotide was derived, or, if from the same/analogous species, one or both are modified from their original form and/or genomic locus, or the promoter is not the native promoter for the operably linked polynucleotide.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, and/or substitutions, e.g., transitions and transversions, may be involved.

The expression cassette can also comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glyphosate, glufosinate ammonium, bromoxynil, or sulfonylureas. Additional selectable markers include phenotypic markers such as β-galactosidase and fluorescent proteins such as green fluorescent protein (GFP) (Su et al. (2004) *Biotechnol Bioeng* 85:610-9 and Fetter et al. (2004) *Plant Cell* 16:215-28), cyan florescent protein (CYP) (Bolte et al. (2004) *J. Cell Science* 117:943-54 and Kato et al. (2002) *Plant Physiol* 129:913-42), and yellow florescent protein (PhiYFP™ from Evrogen, see, Bolte et al. (2004) *J. Cell Science* 117:943-54). For additional selectable markers, see generally, Yarranton (1992) *Curr. Opin. Biotech.* 3:506-511; Christopherson et al. (1992) *Proc. Natl. Acad Sci. USA* 89:6314-6318; Yao et al. (1992) *Cell* 71:63-72; Reznikoff (1992) *Mol. Microbiol.* 6:2419-2422; Barkley et al. (1980) in *The Operon*, pp. 177-220; Hu et al. (1987) *Cell* 48:555-566; Brown et al. (1987) *Cell* 49:603-612; Figge et al. (1988) *Cell* 52:713-722; Deuschle et al. (1989) *Proc. Natl. Acad Aci. USA* 86:5400-5404; Fuerst et al. (1989) *Proc. Natl. Acad Sci. USA* 86:2549-2553; Deuschle et al. (1990) *Science* 248:480-483; Gossen (1993) Ph.D. Thesis, University of Heidelberg; Reines et al. (1993) *Proc. Natl. Acad Sci. USA* 90:1917-1921; Labow et al. (1990) *Mol. Cell. Biol.* 10:3343-3356; Zambretti et al. (1992) *Proc. Natl. Acad Sci. USA* 89:3952-3956; Baim et al. (1991) *Proc. Natl. Acad Sci. USA* 88:5072-5076; Wyborski et al. (1991) *Nucleic Acids Res.* 19:4647-4653; Hillenand-Wissman (1989) *Topics Mol. Struc. Biol.* 10:143-162; Degenkolb et al. (1991) *Antimicrob. Agents Chemother.* 35:1591-1595; Kleinschnidt et al. (1988) *Biochemistry* 27:1094-1104; Bonin (1993) Ph.D. Thesis, University of Heidelberg; Gossen et al. (1992) *Proc. Natl. Acad. Sci. USA* 89:5547-5551; Oliva et al. (1992) *Antimicrob. Agents Chemother.* 36:913-919; Hlavka et al. (1985) *Handbook of Experimental Pharmacology*, Vol. 78 (Springer-Verlag, Berlin); Gill et al. (1988) *Nature* 334:721-724. Such disclosures are herein incorporated by reference in their entirety. The above list of selectable marker genes is not meant to be limiting.

Additional selectable markers that can be employed include those disclosed in WO2016/100804, which is incorporated by reference in its entirety.

iii. Transformation Vectors

The recombinant DNA construct comprising the integration facilitating sequences of SEQ ID NO:1 and/or 2 or an active variant or fragment thereof operably linked to the polynucleotide of interest can be contained in a plasmid or vector. General methods for preparing plasmids or vectors that contain desired genetic components that can be used to transform host cells, including plants, and methods of making those vectors are known. Vectors typically consist of a number of genetic components, including, but not limited to, regulatory elements such as promoters, leaders, introns, and terminator sequences. Regulatory elements are also referred to as cis- or trans-regulatory elements, depending on the proximity of the element to the sequences or gene(s) they control. The promoter region contains a sequence of bases that signals RNA polymerase to associate with the DNA and to initiate the transcription into mRNA using one of the DNA strands as a template to make a corresponding complementary strand of RNA.

The plasmid or vectors may also contain the plasmid backbone DNA segments that provide replication function and antibiotic selection in bacterial cells, for example, an *Escherichia coli* origin of replication such as ori322, a broad host range origin of replication such as oriV or oriRi, and a coding region for a selectable marker such as Spec/Strp that encodes for Tn7 aminoglycoside adenyltransferase (aadA) conferring resistance to spectinomycin or streptomycin, or a gentamicin (Gm, Gent) selectable marker gene.

A "transformation platform" should be understood to mean the genetic machinery required to transfer a gene into cell. Thus, this term encompasses both the transformation vector, the bacteria competent for the transformation of the host cell, and any other components required for stable integration of the polynucleotide of interest into the genome of the host cell. Such components are discussed in further detail elsewhere herein.

In one embodiment, the transformation platform is a unitary transformation vector useful for the transformation of plants, or a unitary plant transformation vector. In this specification, the term "unitary (transformation) vector" generally means a single transformation vector comprising a disarmed Ti plasmid and a transgene and ideally the required number of virulence genes for plant transformation. In another embodiment, the transformation vector is a binary vector system. The term "binary vector system" is taken to mean a two vector system, comprising a first plasmid, which may also be referred to as the plant transformation vector, which comprises expression cassettes for transferring into a plant cell, and second plasmid, also referred to as a helper plasmid, which is a disarmed Ti plasmid that does not carry the T-DNA insert but does containing the necessary virulence (vir) genes to accommodate successful plant transformation.

In other embodiments, the unitary transformation vector comprises a disarmed Ti plasmid (that lacks the native T-DNA borders) and comprises expression cassettes for the T-DNA and the required number of virulence genes. In another embodiment, the binary vector system comprises a binary vector which lacks T-DNA borders and comprises expression cassettes for transferring into a plant cell, and a disarmed Ti plasmid comprising the necessary vir genes to accommodate successful plant transformation. In further embodiments, the binary vector system comprises a binary vector which lack T-DNA borders and comprises SEQ ID NO: 1 and/or SEQ ID NO: 2 and also comprises expression cassettes for transferring into a plant cell, and a disarmed Ti plasmid comprising the necessary vir genes to accommodate successful plant transformation.

II. Host Cells, Plants, Plant Parts, Seeds

By "host cell" is meant a cell which comprises the recombinant DNA construct provided herein. Host cells may be prokaryotic cells or eukaryotic cells. No attempt to describe in detail the various methods known for providing sequences in prokaryotes or eukaryotes will be made.

Various bacterium can be used as a delivery system for the recombinant DNA construct comprising a polynucleotide of interest operably linked to SEQ ID NO: 1 and/or SEQ ID NO:2, or an active variant or fragment thereof into the plant cell. In some embodiments, the bacterium is a member of the order Rhizobiales. This includes the taxonomic families Rhizobiaceae, Phyllobacteriaceae, Brucellaceae, Bradyrhizobiaceae, and Xanthobacteraceae. Although *A. tumefaciens* and *A. rhizogenes* are commonly used as delivery systems for recombinant DNA, both are known plant pathogens. Using plant pathogens to create commercial transgenic plants can prohibitively increase the cost of deregulating these plant. Therefore, the use of other bacterial delivery systems are contemplated. In some embodiments, the bacterium is an *Agrobacterium* spp., but the bacterium is not derived from a strain of *A. tumefaciens* or *A. rhizogenes*. In some embodiments, the bacterium is a *Rhizobium* sp., *Sinorhizobium* sp. (also referred to as *Ensifer* sp.), *Mesorhizobium* sp. *Ochrobactrum* sp., *Bradyrhizobium* sp. or *Azorhizobium* sp.

In other embodiments, the host bacterial strain can be an *Ochrobactrum* sp., such as *O. cytisi, O. daejeonense, O. lupine, O. oryzae, O. trici,* LBNL 124-A-10, HTG3-C-07, *O. pectoris,* and *O. haywardense*. In further embodiments, the host bacterial strain is *O. haywardense* H1 deposited under NRRL B-67078 (see US2018/0216123, incorporated by reference in its entirety herein).

In still other non-limiting embodiments, the host bacterial strain is from *Sinorhizobium meliloti*, such as for example *S. meliloti* SD630 and *S. meliloti* USDA1002. In other embodiments, the host bacterial strain is *Sinorhizobium fredii*, such as for example *Sinorhizobium fredii* SF4404 and *Sinorhizobium fredii* SF542C. In other embodiments, the host bacterial strain is *Bradyrhizobium japonicum*, such as for example *B. japonicum* USDA 6 and *B. japonicum* USDA 110 In other embodiments, the host bacterial strain is *Mesorhizobium loti*, such as for example *M. loti* ML542G and *M. loti* ML4404. In other embodiments, the host bacterial strain is *Rhizobium leguminosarum*, such as for example *R. leguminosarum* USDA2370 and *R. leguminosarum* USDA2408. See, for example, WO2007/137075 which is herein incorporated by reference in its entirety.

Non-limiting examples of recombinant DNA constructs contained within these various bacterium include (a) a construct comprising SEQ ID NO: 2 or an active variant or fragment thereof operably linked 3' to the polynucleotide of interest; (b) a construct comprising SEQ ID NO: 1 and SEQ ID NO: 2 or an active variant or fragment thereof wherein SEQ ID NO: 1 and SEQ ID NO:2 are operably linked to and flank the polynucleotide sequence of interest; (c) a construct comprising SEQ ID NO: 2 or an active variant or fragment thereof operably linked 3' to the polynucleotide of interest and SEQ ID NO: 1 or active variant thereof is operably linked 5' to the polynucleotide of interest. In further embodiments, the recombinant DNA construct and/or the plant transformation vector does not contain a right and/or a left T-DNA border.

In other embodiments, the host cell is a plant cell. It is understood, that upon integration of the recombinant DNA construct into the genomic DNA of the plant cell a footprint (or fragment) of SEQ ID NO: 1 and/or 2 may be integrated into the genome of the host plant cell. Thus, various plants, plant cells, and seeds having such a footprint are provided herein.

As used herein, the term plant includes plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like. Grain is intended to mean the mature seed produced by commercial growers for purposes other than growing or reproducing the species. Progeny, variants, and mutants of the regenerated plants are also included within the scope of the invention, provided that these parts comprise the introduced polynucleotides of interest and a least a footprint of SEQ ID NO: 1 and/or 2 or a variant or fragment thereof.

As used herein, a "footprint" of SEQ ID NO: 1 and/or 2 comprises or consist of at least 8, 9, 10, 11, 12, 13, 14, 15, 16, 17, 18, 19, 20, 21, 22, 23, 24, or 25 contiguous nucleotides of SEQ ID NO: 1 and/or 2 or a variant thereof, wherein said footprint is contiguous with the expression vector comprising the polynucleotide of interest. In specific embodiments, the footprint comprises at least a 5' fragment of the right bookend and/or at least a 3' fragment of the left bookend, wherein said footprint is contiguous with the expression vector comprising the polynucleotide of interest.

Any plant species can be used in the methods and compositions disclose herein, including, but not limited to, monocots and dicots. Examples of plant species of interest include, but are not limited to, corn (*Zea mays*), *Brassica* spp. (e.g., *B. napus, B. rapa, B. juncea*), particularly those *Brassica* species useful as sources of seed oil, alfalfa (*Medicago sativa*), rice (*Oryza sativa*), rye (*Secale cereale*), Sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (Carthamus tinctorius), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), *Citrus* trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), Macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), Hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and *Chrysanthemum*.

Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*), and Poplar and *Eucalyptus*. In specific embodiments, plants of the present invention are crop plants (for example, corn, alfalfa, sunflower, *Brassica*, soybean, cotton, safflower, peanut, sorghum, wheat, millet, tobacco, etc.). In other embodiments, corn and soybean plants are of interest.

A "subject plant or plant cell" is one in which genetic alteration, such as transformation, has been affected as to a gene of interest, or is a plant or plant cell which is descended from a plant or cell so altered and which comprises the alteration. A "control" or "control plant" or "control plant cell" provides a reference point for measuring changes in phenotype of the subject plant or plant cell.

A control plant or plant cell may comprise, for example: (a) a wild-type plant or cell, i.e., of the same germplasm, variety or line as the starting material for the genetic alteration which resulted in the subject plant or cell; (b) a plant or plant cell of the same genotype as the starting material but which has been transformed with a null construct (i.e. with a construct which has no known effect on the trait of interest, such as a construct comprising a marker gene); (c) a plant or plant cell which is a non-transformed segregant among progeny of a subject plant or plant cell; (d) a plant or plant cell genetically identical to the subject plant or plant cell but which is not exposed to conditions or stimuli that would induce expression of the gene of interest; or (e) the subject plant or plant cell itself, under conditions in which the gene of interest is not expressed.

In other embodiments, the host cell can comprise a prokaryotic cell, a eukaryotic cell, a fungus, or bacteria.

III. Method of Introducing

Various methods can be used to introduce the recombinant DNA construct into a host cell, plant or plant part. "Introducing" is intended to mean presenting to the host cell, plant, plant cell or plant part the polynucleotide or polypeptide in such a manner that the sequence gains access to the interior of a cell.

"Stable transformation" is intended to mean that the nucleotide construct introduced into a host cell or plant integrates into the genome of the host cell or plant and is capable of being inherited by the progeny thereof. "Transient transformation" is intended to mean that a polynucleotide is introduced into the host cell or plant and does not integrate into the genome of the host cell or plant or a polypeptide is introduced into a host cell or plant.

Various methods are provided to transform a plant cell. The methods comprise introducing into the plant cell the polynucleotide of interest by bacterially mediated transformation, wherein the bacteria is competent for the transformation of the plant cell and the bacteria comprises a plant transformation vector comprising a recombinant DNA construct comprising a polynucleotide of interest operably linked to one or more of the sequence that facilitate DNA integration disclosed herein.

Transformation protocols as well as protocols for introducing polypeptides or polynucleotide sequences into plants may vary depending on the type of plant or plant cell, i.e., monocot or dicot, targeted for transformation. Suitable methods of introducing polypeptides and polynucleotides into plant cells include microinjection (Crossway et al. (1986) *Biotechniques* 4:320-334), electroporation (Riggs et al. (1986) *Proc. Natl. Acad. Sci. USA* 83:5602-5606, *Agrobacterium*-mediated transformation (U.S. Pat. Nos. 5,563,055 and 5,981,840), direct gene transfer (Paszkowski et al. (1984) *EMBO J.* 3:2717-2722), and ballistic particle acceleration (see, for example, U.S. Pat. Nos. 4,945,050; 5,879,918; 5,886,244; and, 5,932,782; Tomes et al. (1995) in *Plant Cell, Tissue, and Organ Culture: Fundamental Methods*, ed. Gamborg and Phillips (Springer-Verlag, Berlin); McCabe et al. (1988) *Biotechnology* 6:923-926); and Lec1 transformation (WO 00/28058). Also see Weissinger et al. (1988) *Ann. Rev. Genet.* 22:421-477; Sanford et al. (1987) *Particulate Science and Technology* 5:27-37 (onion); Christou et al. (1988) *Plant Physiol.* 87:671-674 (soybean); McCabe et al. (1988) *Bio/Technology* 6:923-926 (soybean); Finer and McMullen (1991) *In Vitro Cell Dev. Biol.* 27P: 175-182 (soybean); Singh et al. (1998) *Theor. Appl. Genet.* 96:319-324 (soybean); Datta et al. (1990) *Biotechnology* 8:736-740 (rice); Klein et al. (1988) *Proc. Natl. Acad. Sci. USA* 85:4305-4309 (maize); Klein et al. (1988) *Biotechnology* 6:559-563 (maize); U.S. Pat. Nos. 5,240,855; 5,322,783; and, 5,324,646; Klein et al. (1988) *Plant Physiol.* 91:440-444 (maize); Fromm et al. (1990) *Biotechnology* 8:833-839 (maize); Hooykaas-Van Slogteren et al. (1984) *Nature (London)* 311:763-764; U.S. Pat. No. 5,736,369 (cereals); Bytebier et al. (1987) *Proc. Natl. Acad. Sci. USA* 84:5345-5349 (Liliaceae); De Wet et al. (1985) in *The Experimental Manipulation of Ovule Tissues*, ed. Chapman et al. (Longman, New York), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); Li et al. (1993) *Plant Cell Reports* 12:250-255 and Christou and Ford (1995) *Annals of Botany* 75:407-413 (rice); Osjoda et al. (1996) *Nature Biotechnology* 14:745-750 (maize via *Agrobacterium tumefaciens*); all of which are herein incorporated by reference in their entirety.

In other instances, the method of transformation employed for soybean is set forth in U.S. Pat. No. 7,473,822 and/or Paz et. al. (2010) "*Agrobacterium-mediated transformation of soybean and recovery of transgenic soybean plants*" Plant Transformation Facility at University of Iowa, 1-6, both of which are herein incorporated by reference in their entirety.

In other embodiments, the recombinant DNA construct comprising a polynucleotide of interest operably linked to one or more of the sequences that facilitate DNA integration disclosed herein may be introduced into plants by contacting plants with a virus or viral nucleic acids. Generally, such methods involve incorporating a nucleotide construct of the invention within a DNA or RNA molecule. It is recognized that the sequence may be initially synthesized as part of a viral polyprotein, which later may be processed by proteolysis in vivo or in vitro to produce the desired recombinant protein. Further, it is recognized that promoters of the invention also encompass promoters utilized for transcription by viral RNA polymerases. Methods for introducing polynucleotides into plants and expressing a protein encoded therein, involving viral DNA or RNA molecules, are known in the art. See, for example, U.S. Pat. Nos. 5,889,191, 5,889,190, 5,866,785, 5,589,367, 5,316,931, and Porta et al. (1996) *Molecular Biotechnology* 5:209-221; herein incorporated by reference in their entirety.

After the construction of the plant transformation vector or construct, the nucleic acid molecule, prepared as a DNA composition in vitro, is generally introduced into a suitable host such as *Escherichia coli* and mated into another suitable host or electroporated directly into a suitable host (i.e., a bacteria competent for plant transformation) such as, but not limited to, *Rhizobium* spp., *Sinorhizobium* spp. (also referred to as *Ensifer* spp.), *Mesorhizobium* spp., *Ochrobactrum* spp., *Bradyrhizobium* spp. or *Azorhizobium* spp. These techniques are known to those of skill in the art and have been described for a number of plant systems including soybean, cotton, and wheat (see, for example, U.S. Pat. Nos. 5,569,834 and 5,159,135 and WO 97/48814).

In one embodiment, the vector is then introduced into a plant cell by bacterially mediated transformation. The given bacteria employed in such methods is competent for the transformation of the plant cell. Plant tissue to be transformed is typically inoculated and co-cultured with a bacteria competent for plant transformation which contains a recombinant construct comprising at least one heterologous DNA integration facilitating (SEQ ID NO: 1 and/or 2 or an active variant or fragment thereof) operably linked to a polynucleotide sequence of interest to be transferred. Transformed cell are selected under appropriate conditions.

In other embodiments, the vector can be introduced into a host cell of interest by bacterially mediated transformation. The given bacteria employed in such methods is competent for the transformation of the host cell.

The recombinant DNA constructs comprising at least one heterologous DNA integration facilitating (SEQ ID NO: 1 and/or 2 or an active variant or fragment thereof) operably linked to a polynucleotide sequence of interest or plasmids and vector comprising the same can be used with any transformable cell or tissue. Transformable plant tissue generally refers to tissue that can have exogenous DNA inserted in its genome and under appropriate culture conditions can form into a differentiated plant. Such tissue can include, but is not limited to, cell suspensions, callus tissue, hypocotyl tissue, cotyledons, embryos, meristematic tissue, roots, and leaves. For example, transformable tissues can include calli or embryoids from anthers, microspores, inflorescences, and leaf tissues.

Methods for transforming plants by use of a bacterial mediated transformation and obtaining transgenic plants have been published for a number of crops including in dicots and monocots. Such plants include, for example, cotton, soybean, *Brassica*, peanut, asparagus, barley, maize, oat, rice, sugarcane, tall fescue, and wheat. See for example, methods for use in the context of cotton transformation are disclosed in U.S. Pat. Nos. 5,846.797, 5,159,135, 5,004,863, and 6,624,344; methods for use for transforming *Brassica* plants are disclosed, for example, in U.S. Pat. No. 5,750, 871; methods for the use of techniques for transforming soybean are disclosed in for example in Zhang et al., (1999) and U.S. Pat. No. 6,384,301; and methods for transforming corn are disclosed in for example in U.S. Pat. Nos. 5,981, 840, 7,060,876, 5,591,616, WO95/06722, and U.S. Patent Pub. 2004/244075. Each of these references is herein incorporated by reference in their entirety.

In one embodiment, after incubation on medium containing antibiotics to inhibit bacterial growth without selective agents, the explants are cultured on selective growth medium including, but not limited to, a callus-inducing medium containing a plant cell selective agent. Typical selective agents have been described and include, but are not limited to, antibiotics such as G418, paromomycin, kanamycin, or other chemicals such as glyphosate, dicamba, and glufosinate. The plant tissue cultures surviving the selection medium are subsequently transferred to a regeneration medium suitable for the production of transformed plantlets. Regeneration can be carried out over several steps. Those of skill in the art are aware of the numerous types of media and transfer requirements that can be implemented and optimized for each plant system for plant transformation and regeneration.

The transformants produced are subsequently analyzed to determine the presence or absence of a particular nucleic acid of interest contained on the transformation vector. The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting progeny having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a polynucleotide of the invention, for example, an expression cassette of the invention, stably incorporated into their genome.

IV. Sequence Comparisons

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller (1988) *CABIOS* 4:11-17; the local alignment algorithm of Smith et al. (1981) *Adv. Appl. Math.* 2:482; the global alignment algorithm of Needleman and Wunsch (1970) *J Mol. Biol.* 48:443-453; the search-for-local alignment method of Pearson and Lipman (1988) *Proc. Natl. Acad. Sci.* 85:2444-2448; the algorithm of Karlin and Altschul (1990) *Proc. Natl. Acad. Sci. USA* 872264, modified as in Karlin and Altschul (1993) *Proc. Natl. Acad. Sci. USA* 90:5873-5877.

Computer implementations of these mathematical algorithms can be utilized for comparison of sequences to determine sequence identity. Additional mathematical algorithms are known in the art and can be utilized for the comparison of two sequences. See, for example, the algorithm of Karlin and Altschul (1990) Proc. Natl. Acad. Sci. USA 87:2264, modified as in Karlin and Altschul (1993) Proc. Natl. Acad. Sci. USA 90:5873-5877. Such an algorithm is incorporated into the BLAST programs of Altschul et al. (1990) J. Mol. Biol. 215:403. BLAST nucleotide searches can be performed with the BLASTN program. BLAST protein searches can be performed with the BLASTP program. To obtain gapped alignments for comparison purposes, Gapped BLAST (in BLAST 2.0) can be utilized as described in Altschul et al. (1997) Nucleic Acids Res. 25:3389. Alternatively, PSI-Blast can be used to perform an iterated search that detects distant relationships between molecules. See Altschul et al. (1997) supra. When utilizing BLAST, Gapped BLAST, and PSI-Blast programs, the default parameters of the respective programs (e.g., BLASTX and BLASTN) can be used. Alignment may also be performed manually by inspection.

As used herein, the term "identity" or "percent identity" when used with respect to a particular pair of aligned amino acid or nucleotide sequences, refers to the percent amino acid sequence identity or the percent nucleotide sequence identity that is obtained by counting the number of identical matches in the alignment and dividing such number of identical matches by the length of the aligned sequences. As used herein, the term "similarity" or "percent similarity" when used with respect to a particular pair of aligned amino acid sequences or nucleotides sequences, refers to the sum of the scores that are obtained from a scoring matrix for each amino acid pair in the alignment divided by the length of the aligned sequences.

Unless otherwise stated, identity and similarity will be calculated by the Needleman-Wunsch global alignment and scoring algorithms (Needleman and Wunsch, 1970, J. Mol. Biol. 48(3):443-453) as implemented by the "needle" program, distributed as part of the EMBOSS software package (Rice, P. Longden, I. and Bleasby, A., EMBOSS: The European Molecular Biology Open Software Suite, 2000, Trends in Genetics 16, (6) pp 276-277, versions 6.3.1 available from EMBnet at EMBOSS web sites, among other sources) using default gap penalties and scoring matrices (EBLOSUM62 for protein and EDNAFULL for DNA). Equivalent programs may also be used. By "equivalent program" is intended any sequence comparison program that, for any two sequences in question, generates an alignment having identical nucleotide residue matches and an identical percent sequence identity when compared to the corresponding alignment generated by needle from EMBOSS version 6.3.1.

The article "a" and "an" are used herein to refer to one or more than one (i.e., to at least one) of the grammatical object of the article. By way of example, "an element" means one or more element.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Units, prefixes, and symbols may be denoted in their SI accepted form. Unless otherwise indicated, nucleic acids are written left to right in 5' to 3' orientation; amino acid sequences are written left to right in amino to carboxy orientation, respectively. Numeric ranges are inclusive of the numbers defining the range. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes. The above-defined terms are more fully defined by reference to the specification as a whole.

Non-Limiting Embodiments Include:

1. A bacterium, which is not an *Agrobacterium* spp., comprising a recombinant DNA construct comprising a polynucleotide of interest operably linked to SEQ ID NO: 1 or SEQ ID NO:2, or an active variant thereof comprising a sequence having at least 92% sequence identity to SEQ ID NO: 1 or 2, wherein said active variant facilitates integration of the polynucleotide of interest into DNA.

2. The bacterium of embodiment 1, wherein SEQ ID NO: 2 or the active variant thereof is 3' to the polynucleotide of interest.

3. The bacterium of embodiment 1, wherein SEQ ID NO: 1 and SEQ ID NO: 2 or the active variant thereof flank the polynucleotide sequence of interest.

4. The bacterium of embodiment 3, wherein SEQ ID NO: 2 or the active variant thereof is 3' to the polynucleotide of interest and SEQ ID NO:1 or the active variant thereof is 5' to the polynucleotide of interest.

5. The bacterium of any one of embodiments 1-4, wherein said DNA construct does not contain a T-DNA border sequence.

6. The bacterium of embodiment 1, wherein the recombinant DNA construct is a plant transformation vector.

7. The bacterium of any one of embodiments 1-6, wherein the bacterium is a *Rhizobium* spp., *Sinorhizobium* spp., *Ensifer* spp., *Mesorhizobium* spp., *Ochrobactrum* spp., *Bradyrhizobium* spp. or *Azorhizobium* spp.

8. The bacterium of embodiment 7, wherein the bacterium is an *Ochrobactrum* spp.

9. The bacterium of embodiment 8, wherein the bacterium is *O. cytisi, O. daejeonense, O. lupine, O. oryzae, O. trici,* LBNL 124-A-10, HTG3-C-07, *O. pectoris,* or *O. haywardense.*

10. The bacterium of embodiment 9, wherein the bacterium from the strain *O. haywardense*H1, deposited under NRRL B-67078.

11. A method of introducing into a plant cell a polynucleotide of interest comprising contacting the plant cell with a bacterium competent for the transformation of the plant cell, where the bacterium is not an *Agrobacterium* spp. and comprises a plant transformation vector comprising a recombinant DNA construct comprising a polynucleotide of interest operably linked to SEQ ID NO: 1 or SEQ ID NO:2 or an active variant thereof comprising a sequence having at least 92% sequence identity to SEQ ID NO: 1 or 2, wherein said active variant facilitates integration of the polynucleotide of interest into DNA.

12. The method of embodiment 11 further comprising selectively screening for a plant cell having integrated the polynucleotide of interest into its genome.

13. The method of embodiment 11 or 12, further comprising isolating a plant cell having the polynucleotide of interest integrated in its genome.

14. The method of any one of embodiments 11-13, wherein SEQ ID NO: 2 or the active variant thereof is 3' to the polynucleotide of interest.

15. The method of any one of embodiments 11-13, wherein SEQ ID NO: 1 and SEQ ID NO: 2 or the active variant thereof flank the polynucleotide sequence of interest.

16. The method of embodiment 15, wherein SEQ ID NO: 2 or the active variant thereof is 3' to the polynucleotide of interest and SEQ ID NO:1 or the active variant thereof is 5' to the polynucleotide of interest.

17. The method of any one of embodiments 11-16, wherein said DNA construct does not contain a T-DNA border sequence.

18. The method of any one of embodiments 11-17, wherein the bacterium is a *Rhizobium* spp., *Sinorhizobium* spp., *Ensifer* spp., *Mesorhizobium* spp., *Ochrobactrum* spp., *Bradyrhizobium* spp. or *Azorhizobium* spp.

19. The method of embodiment 18, wherein the bacterium is an *Ochrobactrum* spp.

20. The method of embodiment 19, wherein the bacterium is *O. cytisi, O. daejeonense, O. lupine, O. oryzae, O. trici,* LBNL 124-A-10, HTG3-C-07, *O. pectoris,* or *O. haywardense.*

21. The method of embodiment 20, wherein the bacterium from the strain *O. haywardense*H1, deposited under NRRL B-67078.

22. The method of any one of embodiments 11-21, wherein said plant cell is from a monocot.

23. The method of embodiment 22, wherein said monocot is maize, wheat, rice, barley, sorghum, or rye.

24. The method of any one of embodiments 11-21, wherein said plant cell is a from a dicot.

25. The method of embodiment 24, wherein said dicot is soybean, *Brassica*, sunflower, cotton, or alfalfa.

EXPERIMENTAL

Example 1: Vector Design

SEQ ID NO: 1 and/or SEQ ID NO: 2, also referred to as Bookend 1 and Bookend 2, may be introduced into a vector useful for transformation of plants. SEQ ID NO: 3 provides the sequence of a DNA construct comprising the bookends and polynucleotide sequences of interest for introduction into plants. A polynucleotide sequence of interest for introduction into plants comprises at least one expression cassette and is also referred to as a DNA insert. Similarly constructed DNA constructs may have (1) both Bookends flanking the DNA insert or (2) having Bookend 1 operably linked to the 5' end of the DNA insert and Bookend 2 operably linked to the 3' of the insert, or (3) just Bookend 2 only operably linked to the 3' end of the DNA insert.

Figure 1:
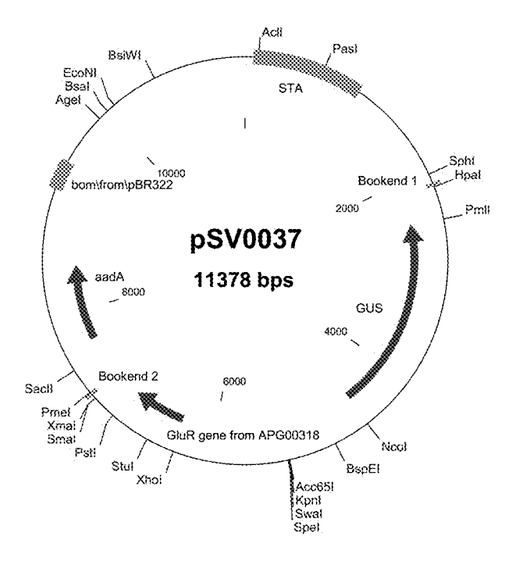
FIG. 1 provides a map of the transformation vector pSV0037.

As described above, bacteria-mediated plant transformation requires a transformation platform. One example of a transformation platform is the binary vector system. In addition to a binary vector, a disarmed Ti plasmid which comprises the vir genes needed for successful plant transformation is required. An example of a disarmed Ti plasmid, also referred to as a helper plasmid, is pEHA105, which is derived from pTiBO542 (see Hood et al., 1993, *Transgenic Research*, 2: 208-218). Vector pSV0037 (see FIG. 1) is a binary vector comprising Bookend 1 and Bookend 2 flanking a DNA insert that comprises expression cassettes which comprise a GUS reporter gene and a glufosinate resistance gene as a selectable marker for plant transformation.

Alternatively, the transformation platform may comprise a single vector with the DNA insert and the vir genes present on the same plasmid, which is referred to as a unitary transformation vector. An example of a unitary vector comprising the vir genes and the DNA insert is SEQ ID NO: 4, which is referred to here as pC5105-bookend. pC5105-bookend is based on the pCAMBIA 5105 unitary transformation vector, which is described in US 2009/0075358 (incorporated by reference in its entirety herein). pC5105 comprises SEQ ID NO: 1 operably linked to the 5' end of the DNA insert and SEQ ID NO: 2 operably linked to the 3' end of the DNA insert.

Example 2: *Ochrobactrum*-Mediated Transformation of Soybean

This example describes transformation of a soybean plant cell using an *Ochrobactrum* sp.

The pC5105-bookend vector (comprising SEQ ID NO: 4) is introduced into an *Ochrobactrum* sp. cell. The *Ochrobactrum* sp. may be, for example, *O. cytisi, O. daejeonense, O. lupine, O. oryzae, O. trici*, LBNL 124-A-10, HTG3-C-07, *O. pectoris*, or *O. haywardense*. The *Ochrobactrum* sp. may be strain *O. haywardense*H1, deposited under NRRL B-67078. pC5105-bookend is introduced into the *Ochrobactrum* sp. using methods well-known in the art (See for example US 2018/0216123). The DNA insert of the pC5105-bookend vector comprises two gene cassettes, one which contains a hygromycin resistance selectable marker for selection of plant or plant cell transformants and a second gene cassette which contains the GusPlus™ gene for screening for expressing transgenic plants or plant cells.

Alternatively, the helper plasmid pEHA105 and the pSV0037 vector (comprising SEQ ID NO: 3) are co-introduced into an *Ochrobactrum* sp. cell. The *Ochrobactrum* sp. may be, for example, *O. cytisi, O. daejeonense, O. lupine, O. oryzae, O. trici*, LBNL 124-A-10, HTG3-C-07, *O. pectoris*, or *O. haywardense*. The *Ochrobactrum* sp. may be strain *O. haywardense* H1, deposited under NRRL B-67078. The DNA insert of the pSV0037 vector comprises two gene cassettes, one cassette which contains a glufosinate resistant selectable marker, and a second gene cassette which contains a GUS gene for screening for expressing transgenic plants or plant cells.

*Ochrobactrum* sp. carrying either pC5105 or pSV0037 and pEHA105 are grown to an OD600=0.5 as described in US 2018/0216123. Soybean transformation is performed essentially as described by Paz et al. (2006, *Plant Cell Rep.* 25:206-213) and in U.S. Pat. No. 7,473,822, both of which are incorporated by reference in their entirety herein.

Transgenic soybean plant cells transformed with the pC5105-bookends vector are selected by incubating callus pieces on media containing hygromycin. Transgenic soybean plant cells transformed with the pSV0037 vector are selected by incubating callus on 25 µM glufosinate containing media. Expression of the DNA insert by the transgenic calli is determined by staining the callus pieces with GUS stain.

Recovery of transgenic calli and regeneration of transgenic soybean plants is performed essentially as described by Paz et al. (2006, Plant Cell Rep. 25:206-213), U.S. Pat. No. 7,473,822, and Paz et al. (2010) *Agrobacterium*-mediated transformation of soybean and recovery of transgenic soybean plants; Plant Transformation Facility of Iowa State University, which is herein incorporated by reference in its entirety.

Although the foregoing invention has been described in some detail by way of illustration and example for purposes of clarity of understanding, it will be obvious that certain changes and modifications may be practiced within the scope of the appended claims.

That which is claimed:

1. A bacterium, which is not an *Agrobacterium* spp., comprising a recombinant DNA construct comprising a polynucleotide of interest operably linked to SEQ ID NO: 1 or SEQ ID NO:2, or an active variant thereof comprising a sequence having at least 92% sequence identity to SEQ ID NO: 1 or 2, wherein said active variant facilitates integration of the polynucleotide of interest into DNA.

2. The bacterium of claim 1, wherein SEQ ID NO: 2 or the active variant thereof is 3' to the polynucleotide of interest.

3. The bacterium of claim 1, wherein SEQ ID NO: 1 and SEQ ID NO: 2 or the active variant thereof flank the polynucleotide sequence of interest.

4. The bacterium of claim 3, wherein SEQ ID NO: 2 or the active variant thereof is 3' to the polynucleotide of interest and SEQ ID NO: 1 or the active variant thereof is 5' to the polynucleotide of interest.

5. The bacterium of claim 1, wherein said DNA construct does not contain a T-DNA border sequence.

6. The bacterium of claim 1, wherein the recombinant DNA construct is a plant transformation vector.

7. The bacterium of claim 1, wherein the bacterium is a *Rhizobium* spp., *Sinorhizobium* spp., Ensifer spp., *Mesorhizobium* spp., Ochrobactrum spp., *Bradyrhizobium* spp. or *Azorhizobium* spp.

8. The bacterium of claim 7, wherein the bacterium is an Ochrobactrum spp.

9. The bacterium of claim 8, wherein the bacterium is *O. cytisi, O. daejeonense, O. lupine, O. oryzae, O. trici tritici,* LBNL 124-A-10, HTG3-C-07, *O. pectoris,* or *O. haywardense.*

10. The bacterium of claim 9, wherein the bacterium from the strain *O. haywardense* H1, deposited under NRRL B-67078.

11. A method of introducing into a plant cell a polynucleotide of interest comprising contacting the plant cell with the bacterium of claim 1 competent for the transformation of the plant cell.

12. The method of claim 11 further comprising selectively screening for a plant cell having integrated the polynucleotide of interest into its genome.

13. The method of claim 11, further comprising isolating a plant cell having the polynucleotide of interest integrated in its genome.

14. The method of claim 11, wherein SEQ ID NO: 2 or the active variant thereof is 3' to the polynucleotide of interest.

15. The method of claim 11, wherein SEQ ID NO: 1 and SEQ ID NO: 2 or the active variant thereof flank the polynucleotide sequence of interest.

16. The method of claim 15, wherein SEQ ID NO: 2 or the active variant thereof is 3' to the polynucleotide of interest and SEQ ID NO: 1 or the active variant thereof is 5' to the polynucleotide of interest.

17. The method of claim 11, wherein said DNA construct does not contain a T-DNA border sequence.

18. The method of claim 11, wherein the bacterium is a *Rhizobium* spp., *Sinorhizobium* spp., Ensifer spp., *Mesorhizobium* spp., Ochrobactrum spp., *Bradyrhizobium* spp. or *Azorhizobium* spp.

19. The method of embodiment 18, wherein the bacterium is an Ochrobactrum spp.

20. The method of claim 19, wherein the bacterium is *O. cytisi*, *O. daejeonense*, *O. lupine*, *O. oryzae*, *O. tritici*, LBNL 124-A-10, HTG3-C-07, *O. pectoris*, or *O. haywardense*.

21. The method of claim 20, wherein the bacterium from the strain O. haywardense H1, deposited under NRRL B-67078.

22. The method of claim 11, wherein said plant cell is from a monocot.

23. The method of claim 22, wherein said monocot is maize, wheat, rice, barley, sorghum, or rye.

24. The method of claim 11, wherein said plant cell is from a dicot.

25. The method of claim 24, wherein said dicot is soybean, *Brassica*, sunflower, cotton, or alfalfa.

* * * * *

SEQUENCE LISTING

<160> NUMBER OF SEQ ID NOS: 3

<210> SEQ ID NO 1
<211> LENGTH: 25
<212> TYPE: DNA
<213> ORGANISM: Sinorhizobium fredii

<400> SEQUENCE: 1
tggcaggata tatgctggtg taaac        25

<210> SEQ ID NO 2
<211> LENGTH: 25
<212> TYPE: DNA
<213> ORGANISM: Sinorhizobium fredii

<400> SEQUENCE: 2
tggcaggata tatgttggtg taacc        25

<210> SEQ ID NO 3
<211> LENGTH: 5110
<212> TYPE: DNA
<213> ORGANISM: Artificial Sequence
<220> FEATURE:
<223> OTHER INFORMATION: DNA construct
<220> FEATURE:
<223> OTHER INFORMATION: bookend 2 (in reverse)
<220> FEATURE:
<223> OTHER INFORMATION: bookend 1 (in reverse)
<220> FEATURE:
<223> OTHER INFORMATION: NOS terminator (in reverse)
<220> FEATURE:
<223> OTHER INFORMATION: GUS gene with intron (in reverse)
<220> FEATURE:
<223> OTHER INFORMATION: CaMV 35S promoter (in reverse)
<220> FEATURE:
<223> OTHER INFORMATION: 2XCaMV 35S Promoter
<220> FEATURE:
<223> OTHER INFORMATION: glufosinate resitance gene
<220> FEATURE:
<223> OTHER INFORMATION: CaMV 35S terminator and polyA

<400> SEQUENCE: 3

```
ggttacacca acatatatcc tgccaaacac tgatagttaa ctaattcccg atctagtaac      60
atagatgaca ccgcgcgcga taatttatcc tagtttgcgc gctatatttt gttttctatc     120
gcgtattaaa tgtataattg cgggactcta atcataaaaa cccatctcat aaataacgtc     180
atgcattaca tgttaattat tacatgctta acgtaattca acagaaatta tatgataatc     240
atcgcaagac cggcaacagg attcaatctt aagaaacttt attgccaaat gtttgaacga     300
tcggggaaat tcgagctggt cacctgtaat tcacacgtgg tggtggtggt ggtggctagc     360
ttgtttgcct ccctgctgcg gttttttcacc gaagttcatg ccagtccagc gttttttgcag    420
cagaaaagcc gccgacttcg gtttgcggtc gcgagtgaag atcccttttct gttaccgcc     480
aacgcgcaat atgccttgcg aggtcgcaaa tcggcgaaa ttccatacct gttcaccgac      540
gacggcgctg acgcgatcaa agacgcggtg atacatatcc agccatgcac actgatactc     600
ttcactccac atgtcggtgt acattgagtg cagcccggct aacgtatcca cgccgtattc     660
ggtgatgata tcggctgat gcagtttctc ctgccaggcc agaagttctt tttccagtac      720
cttctctgcc gtttccaaat cgccgctttg gacataccat ccgtaataac ggttcaggca     780
cagcacatca agagatcgc tgatggtatc ggtgtgagcg tcgcagaaca ttacattgac      840
gcaggtgatc ggacgcgtcg ggtcgagttt acgcgttgct tccgccagtg gcgcgaaata     900
ttcccgtgca ccttgcggac gggtatccgg ttcgttggca atactccaca tcaccacgct     960
tgggtggttt ttgtcacgcg ctatcagctc tttaatcgcc tgtaagtgcg cttgctgagt    1020
ttccccgttg actgcctctt cgctgtacag ttctttcggc ttgttgcccg cttcgaaacc    1080
aatgcctaaa gacagctgaa gccgacagc agcagtttca tcaatcacca cgatgccatg    1140
ttcatctgcc cagtcgagca tctcttcagc gtaagggtaa tgcgaggtac ggtaggagtt    1200
ggccccaatc cagtccatta atgcgtggtc gtgcaccatc agcacgttat cgaatccttt    1260
gccacgtaag tccgcatctt catgacgacc aaagccagta agtagaacg gtttgtggtt     1320
aatcaggaac tgttgcccct tcactgccac tgaccggatg ccgacgcgaa gcgggtagat    1380
atcagactct gtctggcttt tggctgtgac ttcgagttca tagagataac cttcacccgg    1440
ttgccagagg tgcggattca ccacttgcaa agtcccgcta gtgccttgtc cagttgcaac    1500
cacctgttga tccgcatcac gcagttcaac gctgacatca ccattggcca ccacctgcca    1560
gtcaacagac gcgtggttac agtcttgcgc gacatgcgtc accacggtga tatcgtccac    1620
```

```
ccaggtgttc ggcgtggtgt agagcattac gctgcgatgg attccggcat agttaaagaa    1680
atcatggaag taagactgct ttttcttgcc gttttcgtcg gtaatcacca ttcccggcgg    1740
gatagtctgc cagttcagtt cgttgttcac acaaacggtg atacgtacac ttttcccggc    1800
aataacatac ggcgtgacat cggcttcaaa tggcgtatag ccgccctgat gctccatcac    1860
ttcctgatta ttgacccaca ctttgccgta atgagtgacc gcatcgaaac gcagcacgat    1920
acgctggcct gcccaacctt tcggtataaa gacttcgcgc tgataccaga cgttgcccgc    1980
ataattacga atatctgcat cggcgaactg atcgttaaaa ctgcctggca cagcaattgc    2040 ccggcttttct tgtaacgcgc tttcccacca acgctgatca attccacagt tttcgcgatc    2100
cagactgaat gcccacaggc cgtcgagttt tttgatttca cgggttgggg tttctacagg    2160
acggacgagt cgtcggttct gtaactatca tcatcatcat agacacacga aataaagtaa    2220
tcagattatc agttaaagct atgtaatatt tacaccataa ccaatcaatt aaaaaataga    2280
tcagtttaaa gaaagatcaa agctcaaaaa aataaaaaga gaaaagggtc taaccaaga    2340 aaatgaagga gaaaaactag aaatttaccc tcagatctac catggtcaag agtccccgt    2400 gttctctcca aatgaaatga acttccttat atagaggaag ggtcttgcga aggatagtgg    2460
gattgtgcgt catcccttac gtcagtggag atatcacatc aatccacttg ctttgaagac    2520
gtggttggaa cgtcttcttt ttccacgatg ctcctcgtgg gtggggtcc atctttggga    2580 ccactgtcgg cagaggcatc ttcaacgatg gcctttcctt tatcgcaatg atggcatttg    2640
taggagccac cttccttttc cactatcttc acaataaagt gacagatagc tgggcaatgg    2700
aatccgagga ggtttccgga tattacccctt tgttgaaaag tctcaattgc cctttggtct    2760
tctgagactg tatctttgat attttttggag tagacaagtg tgtcgtgctc caccatgttg    2820
acgaagattt tcttcttgtc attgagtcgt aagagactct gtatgaactg ttcgccagtc    2880 tttacgcga gttctgttag gtcctctatt tgaatctttg actccatgaa gctaaactga    2940
aggcgggaaa cgacaatctg atccaagctc aagctgctct agcattcgcc attcaggctg    3000
cgcaactgtt gggaagggcg atcggtgcgg gcctcttcgc tattacgcca gctggcgaaa    3060
gggggatgtg ctgcaaggcg attaagttgg gtaacgccag ggttttccca gtcacgacgt    3120
tgtaaaacga cggccagtgc caagctatct ccatttaaat caacctaatt cgtaatcatg    3180
gtcatagctg tttcctgtgt gaaattgtta tccgctcaca attccacaca atacgagc    3240 cggaagcata aagtgtaaag cctggggtgc ctaatgagtg agctaactca cattaattgc    3300
gttgcgctca ctgcccgctt tccagtcggg aaacctgtcg tgccagctgc attaatgaat    3360
cggccaacgc gcggggagag gcggtttgcg tattggctag agcagcttgc caacatggtg    3420
gagcacgaca ctctcgtcta ctccaagaat atcaaagata cagtctcaga agaccaaagg    3480
gctattgaga cttttcaaca aagggtaata tcgggaaacc tcctcggatt ccattgccca    3540
gctatctgtc acttcatcaa aaggacagta gaaaaggaag gtggcaccta caaatgccat    3600
cattgcgata aaggaaaggc tatcgttcaa gatgcctctg ccgacagtgg tcccaaagat    3660 ggaccccac ccacgaggag catcgtggaa aaagaagacg ttccaaccac gtcttcaaag    3720
caagtggatt gatgtgataa catggtggag cacgacactc tcgtctactc caagaatatc    3780
aaagatacag tctcagaaga ccaaagggct attgagactt tcaacaaag ggtaatatcg    3840 ggaaacctcc tcggattcca ttgcccagct atctgtcact tcatcaaaag gacagtagaa    3900
aaggaaggtg gcacctacaa atgccatcat tgcgataaag gaaaggctat cgttcaagat    3960
```

-continued

```
gcctctgccg acagtggtcc caaagatgga cccccaccca cgaggagcat cgtggaaaaa   4020
gaagacgttc caaccacgtc ttcaaagcaa gtggattgat gtgatatctc cactgacgta   4080
agggatgacg cacaatccca ctatccttcg caagaccttc ctctatataa ggaagttcat   4140
ttcatttgga gaggacacgc tgaaatcacc agtctctctc tacaaatcta tctctctcga   4200
gctttcgcag atctgtcgat cgaccatgag caagacgaca gtaaggattg cgcaggtttc   4260
ggacgctcaa gccatccagg caatctacgc accaatggtt gagagcacta cgatttcgtt   4320
cgagcttgag ccgccttcag tcgaagagat ggccatgcgg attgagtcga ctctgctaac   4380
ttacccgtac ctggttgcgg tgcgagacgg ccaggtcatc ggctatgcat atgccagtca   4440
gcaccgggct cgtgaggcct atcgctggtc ggtcgacgtc accgtttata tatcgccaga   4500
agcgcaccgt agtggcgtcg gtcgggcact gtatgacgtg ttgctgccaa cattgaagaa   4560
gcaaggtttt cacgcagcct atgccgggat cgctctgccc aatgatggca gcgtgggact   4620
acacgaagca cttggcttcg ctcacattgg tacgtatcca gaagtaggat tcaagcatgg   4680
cgcttggcgt gatgttggat attggcgtat cgcgctggat tcaacgaatc cgccaaaact   4740
gcccgtgctt ttcagtgaga tcagtctctt ctgagcggga ctctggggtt cggatcgatc   4800
ctctagctag agtcgatcga caagctcgag tttctccata ataatgtgtg agtagttccc   4860
agataaggga attagggttc ctatagggtt tcgctcatgt gttgagcata taagaaaccc   4920
ttagtatgta tttgtatttg taaaatactt ctatcaataa aatttctaat tcctaaaacc   4980
aaaatccagt actaaaatcc agatcccccg aattaattcg gcgttaattc agtacattaa   5040
aaacgtcccg ggcaatgtgt tattaagttg tctaagcgtc aatttgttta caccagcata   5100
tatcctgcca                                                          5110
```